US012673163B2

(12) United States Patent
Urbanek et al.

(10) Patent No.: US 12,673,163 B2
(45) Date of Patent: Jul. 7, 2026

(54) AUTOINJECTOR WITH A SEPARABLE ELECTRONICS MODULE

(71) Applicant: Ypsomed AG, Burgdorf (CH)

(72) Inventors: Leos Urbanek, Bern (CH); Markus Tschirren, Burgdorf (CH); Gabriel Kalbermatter, Burgdorf (CH); Simon Martin Bosshard, Hindelbank (CH); Dominik Zumstein, Bern (CH); Christian Schrul, Oberburg (CH)

(73) Assignee: Ypsomed AG, Burgdorf (CH)

( * ) Notice: Subject to any disclaimer, the term of this patent is extended or adjusted under 35 U.S.C. 154(b) by 380 days.

(21) Appl. No.: 18/417,263

(22) Filed: Jan. 19, 2024

(65) Prior Publication Data

US 2024/0148975 A1 May 9, 2024

Related U.S. Application Data

(63) Continuation of application No. PCT/EP2022/070549, filed on Jul. 21, 2022.

(30) Foreign Application Priority Data

Jul. 22, 2021 (EP) ..................................... 21187112

(51) Int. Cl.
A61M 5/20 (2006.01)

(52) U.S. Cl.
CPC ... A61M 5/2033 (2013.01); *A61M 2005/2013* (2013.01)

(58) Field of Classification Search
CPC .................. A61M 5/20; A61M 5/2033; A61M 2005/2013
See application file for complete search history.

(56) References Cited

U.S. PATENT DOCUMENTS

2018/0008779 A1* 1/2018 Hautaviita ........ A61M 5/31501
2018/0318526 A1* 11/2018 Yang ................... A61M 5/3204
(Continued)

FOREIGN PATENT DOCUMENTS

EP 2060284 A1 5/2009
EP 4122512 A1 1/2023
(Continued)

OTHER PUBLICATIONS

International Preliminary Report on Patentability issued in International Application No. PCT/EP2022/070549, mailed on Jan. 18, 2024, 5 pages.
(Continued)

*Primary Examiner* — David P. Olynick
(74) *Attorney, Agent, or Firm* — Dorsey & Whitney LLP

(57) ABSTRACT

An injection device for subcutaneously administrating a maximum content of a product container through a cannula at a distal end of the product container, comprising a device housing having an opening at a proximal end, a module housing for covering the opening, which module housing is separable from the device housing by a separating operation, a drive which is arranged in the device housing, for moving an advancing element and for the one-time automatic ejection of the contents of the product container. An electronics module is held in the module housing, with a sensor for detecting the discharging, and a mechanical securing mechanism is provided for enabling the separating operation as or after the automatic ejection is triggered.

13 Claims, 7 Drawing Sheets

(56) References Cited

U.S. PATENT DOCUMENTS

| 2018/0369488 A1* | 12/2018 | Carlsson ............. A61M 5/3157 |
|---|---|---|
| 2019/0022328 A1 | 1/2019 | Schleicher et al. |
| 2019/0022330 A1* | 1/2019 | Schleicher ........ A61M 5/31546 |
| 2020/0179612 A1* | 6/2020 | Wei ................... A61M 5/31571 |
| 2024/0393191 A1* | 11/2024 | Yin ......................... G01L 1/042 |

FOREIGN PATENT DOCUMENTS

| WO | 2016120207 A1 | 8/2016 |
|---|---|---|
| WO | 2017129314 A1 | 8/2017 |
| WO | 2021191095 A1 | 9/2021 |
| WO | 2023001988 A1 | 1/2023 |

OTHER PUBLICATIONS

European Search Report issued in European Patent Application No. 21187112.4, mailed on Jan. 28, 2022, 5 pages.
International Search Report and Written Opinion issued in International Application No. PCT/EP2022/070549, mailed on Oct. 25, 2022, 10 pages including 2 pages of English translation.

* cited by examiner

AUTOINJECTOR WITH A SEPARABLE ELECTRONICS MODULE

CROSS-REFERENCE TO RELATED APPLICATIONS

This application is a continuation of International Application No. PCT/EP2022/070549, filed on Jul. 21, 2022, entitled "AUTOINJECTOR WITH A SEPARABLE ELECTRONICS MODULE," which claims priority to European Patent Application No. 21187112.4 filed Jul. 22, 2021, entitled "AUTOINJECTOR WITH SEPARABLE ELECTRONICS MODULE", each of which is incorporated by reference herein, in their entirety and for all purposes.

TECHNICAL FIELD

The present invention relates to the field of medical injection devices for administering liquid substances, in particular medicaments or medical substances, such as insulin and hormone preparations. The invention relates to an autoinjector with an energy store for ejecting a predetermined dose from a product container that is used one time.

BACKGROUND

Injection devices or injection apparatuses for simplified administrating of a substance inter alia comprise so-called autoinjectors which have an energy store with which the ejection can be carried out automatically, i.e., without a force to be supplied or exerted externally by a user. The energy store advantageously stores the energy required for an automatic substance delivery in mechanical form. Such an energy store can be a spring which is installed in a tensioned state in the injection device and delivers energy by expansion. The energy is delivered to a piston rod or a pressure element, which pushes a piston into a product container. The energy store may also be provided in order to automate the process of inserting an injection needle. Alternatively, the piercing process can be carried out manually, i.e., exclusively by a user, without using energy stored in the injection device for this purpose.

The injection device may comprise a product container holder for accommodating a product container, wherein the product container can be held in the product container holder radially, axially, and preferably also in a rotationally fixed manner. The product container holder may be connected to the housing of the injection apparatus in an axially and rotationally fixed manner or may be movable relative to the housing during an insertion and/or needle retraction process. The product container may be a cartridge for the repeatedly detachable connection to disposable injection needles or a disposable pre-filled syringe with an injection needle non-detachably connected thereto. The product container has a hollow cylindrical product container portion which displaceably mounts a piston or plunger. The piston can form a sealing gap with the inner circumference of the product container portion and can be displaced in a distal direction by means of a piston rod in order to dispense product from the product container via the injection needle.

The injection device may have a needle protection sleeve which, after injection has taken place, projects distally beyond the distal end of the injection needle or is displaced relative to the housing into this position while expanding a needle protection sleeve spring, in order to prevent accidental access to the injection needle and to thereby reduce the risk of injury. In an autoinjector, the needle-guard sleeve can also serve as a trigger element for triggering the product ejection process, wherein the needle-guard sleeve is displaced relative to the housing in the proximal direction for this purpose. Alternatively, the triggering of the autoinjector can be achieved by actuating a trigger button of the autoinjector, wherein the needle-guard sleeve serves at least as a visual protection before the autoinjector is used.

Patent application WO 2021/191095 A1 describes an autoinjector comprising a housing with a longitudinal axis, a product container, a torsion spring pretensioned for one-time ejection of a maximum content of the product container, a drive element, and an advancing element. For ejecting a maximum or at least a predetermined amount of liquid from the product container, the torsion spring causes the drive element to rotate about the longitudinal axis, and the rotating drive element causes an advancing movement of the advancing element to displace a piston in the product container. The autoinjector further comprises a permanently installed rotation sensor for detecting a start of the ejection. The autoinjector comprises a communication unit for communicating with a mobile or stationary third-party device and/or a display unit for displaying a state of the autoinjector. The communication unit and/or the display unit, and an energy source for feeding them are arranged on a printed circuit board, which can be removed from the rest of the autoinjector together with a housing part that can be easily separated from the rest of the autoinjector, preferably by means of predetermined breaking lines in the housing. All of the disposal-critical electronic components of the rotation sensor are preferably also arranged on the printed circuit board so that no electronic components remain in the autoinjector after the printed circuit board has been removed.

Patent application WO 2017/129314 describes an autoinjector with a detector for detecting a start of an ejection based on a movement of a triggering element which is pushed proximally by a needle protection sleeve when the autoinjector is placed on the injection site. As a result of the detection, a communication unit of the autoinjector is activated. A proximal movement of an end click element at the end of the ejection is detected by a second detector. The communication unit is non-detachably connected to the autoinjector or is part of an additional module that can be connected to the autoinjector by the user himself.

SUMMARY

It is an object of the invention to provide an injection device for the automatic ejection of a liquid from a product container with an electronics module that can be reliably separated for separate disposal. The object is achieved by an injection device having the features of the independent claims. Preferred embodiments of the invention are the subject matter of the dependent claims.

According to the invention, the injection device for subcutaneous administrating a maximum or total content of a product container, in particular a dose of a liquid medicament, through a cannula or injection needle preferably non-detachably fastened to a distal end of the product container, comprises the following components:

A device housing having a handle region for gripping and holding the injection device by a user during administration, defining a longitudinal direction, and having an opening for assembly purposes at a proximal end.

A module housing or a module cap for covering or closing the opening of the device housing, which can be separated from the device housing by a separating operation of a user.

A drive arranged in the device housing with an energy store in the form of a pretensioned ejection spring for moving an advancing element in the longitudinal direction and for one-time automatic and preferably non-electric ejection of the contents of the product container.

An electronics module held in the module housing with a sensor for detecting an ejection process, and with a communication unit for wireless transmission of a report on the detected ejection process. The electronics module comprises at least all electronic components of the injection device that are relevant for disposal purposes. With the exception of the product container and metallic components such as mechanical springs or electrical conductors in the form of wires or flexible conductors, only plastic parts of the injection device remain after the separating operation, which can be disposed of with medical waste in a known manner.

According to the invention, the injection device comprises a mechanical securing mechanism for preventing or locking the separating operation prior to the start of the ejection and for releasing or unlocking the separating operation at the earliest as or after the automatic ejection is triggered. This prevents the electronics module from being removed from the injection device before the injection begins, and the detector from being unable to detect the start of the injection. The separating operation is released at the latest with the last step of the injection process, and preferably before the injection device is removed from an injection site. This also ensures that the separating operation is carried out and the electronics module can be separated from the injection device, even if an incorrect manipulation or problems with the needle protection device occur when the injection device is removed from the injection site.

In an advantageous variant, the separating operation comprises a rotating loosening movement of the module housing relative to the device housing, which, similar to a bayonet lock, can be followed by an axial loosening movement, or which, similar to a childproof safety twist lock, can be preceded by an axial loosening movement of the module housing towards the device housing. The separating operation alternatively comprises a purely axial loosening movement of the module housing away from the device housing, for example, to release a snap connection between the module housing and the device housing.

In contrast to a purely rotating or transverse loosening movement, an axial loosening movement of the module housing towards the device housing in particular involves an expenditure of force, which causes a painful movement of the needle in the injection site for the user when the injection device is in place. The user is additionally motivated by the expectation of this pain to wait with the axial loosening movement until after the injection device has been removed from the injection site. The need to use a tool to carry out the separating operation of the module housing released for separation from the device housing can further motivate the user to wait until after the injection before separating the electronics module from the injection device.

In a preferred embodiment, the mechanical securing mechanism comprises a release element in the form of a bracket, a tab, or a latch; either as a stand-alone component, or as a part of a housing insert fixed to the housing, or integrally formed with the module or device housing. In a locking position of the release element, the release element locks or blocks the loosening movement prior to the start of the ejection, and releases the loosening movement as or after the ejection is triggered. For this purpose, the release element assumes a release position prior to the removal of the injection device from the injection site, caused directly by a triggering movement of the user, for example a displacement of the needle protection sleeve when the device is pressed onto the injection site, or by an ejection spring of the drive after triggering, or by a signaling spring for acoustic or tactile signaling of a start or end of the ejection.

The release position is therefore assumed before the injection device is removed from the injection site and is not caused by a needle protection spring expanding distally on this occasion. The release stroke of the release element into the release position is preferably carried out against a pretension of the release element into the locking position, with which a spontaneous release of the separating operation is prevented, wherein the latter can also occur due to axial frictional forces on the release element. Instead of having an immediate effect, the movement of the release element into the release position can also first push an additional locking element into a release position enabling the loosening movement.

In a preferred embodiment, the injection device comprises an ejection spring in the form of a compression spring for driving an advancing element in the form of a piston sleeve, as well as a retaining element for retaining the ejection spring in a pretensioned state before triggering, at the proximal end of which the compression spring is supported. The release element is moved into the release position by a proximal movement of the retaining element, caused by the ejection spring at the beginning or end of the ejection. Alternatively, the injection device comprises an ejection spring in the form of a torsion spring and a rotating drive element in the form of a threaded rod for driving an advancing element in the form of a piston sleeve with an internal thread. The release element is moved into the release position by a proximal movement of the drive element when counter pressure is built up on the advancing element by the liquid in the product container.

In a preferred embodiment, the separating operation comprises an axial loosening movement in the direction of a longitudinal axis of the injection device, wherein the module housing is snapped onto or with the device housing or a housing insert by snap elements, which are prevented from loosening or snapping out of the release element in the locking position via non-axial locking surfaces.

In a preferred embodiment, the separating operation comprises a rotating loosening movement in a plane perpendicular to a longitudinal axis of the injection device. A radially inward-pointing projection on the module housing is prevented from rotating by the release element in the locking position via non-tangential locking surfaces. Alternatively, if the release element itself rotates during the loosening movement, the latter is prevented from rotating in the locking position by a radially inward-pointing projection on the device housing or on a housing insert in the device housing.

In a preferred embodiment, the electronics module comprises a communication unit or a transmitter, and a battery or other energy store for powering the communication unit, which is held in a battery compartment and can only be removed from the electronics module and taken to a specific collection point when the module housing is separated. Preferably, the battery is only slightly or not at all clamped in the battery compartment and falls out of the battery compartment purely due to gravity at or after the separation, wherein it can still be held on a non-tear resistant thread and is therefore not lost. Preferably, the electronics module does not have a display for displaying different alphanumeric characters, but at most a color or light pulse pattern coded optical status display.

In a preferred embodiment, the sensor is designed and/or arranged to detect an axial or radial movement of the retaining element, the drive element or the advancing element caused by the ejection spring. In particular, the movements of the retaining element and of the drive element can take place in the proximal direction counter to the direction of ejection and can be intercepted after a short distance by a support or stop element fixed to the housing. Alternatively, the sensor is designed to detect an axial movement of a needle protection sleeve or a signal element caused by a needle protection spring, in particular the presence or absence of the signal element in its proximal position in contact with a signal stop. A single sensor can detect both the start and the end of the ejection, for example if the signal element is moved away from the signal stop by a clamping stroke at the start of the ejection by the force of the ejection spring and under tension of the needle protection spring. Otherwise, two or more sensors can also be provided. An axial extension in the form of a plunger or pin on said movable elements and/or on the sensor, or realized by a separate switching adapter, can ensure mechanical contact or mutual force fit to the sensor.

The electronics module comprises a processor unit which is switched on from a de-energized state by a mechanical switching detector as a sensor or awakened from an energy-saving mode by an electronic detector as a sensor. The detected ejection, together with a time stamp and further information such as the duration of the ejection or a holding time, is transmitted wirelessly to a mobile device by the communication unit. This transmission can also take place or be terminated after the electronics module has been disconnected. The processor unit can additionally be configured to generate an acoustic or tactile indication to the user, which indicates the expiry of a holding time of a few seconds after the end of the ejection. An exemplary visual feedback on the expiry of the holding time comprises the change of an LED from a flashing state to a stationary state or vice versa, this indication stops at the latest when the injection device is lifted from the injection site.

Preferably, the injection device is an autoinjector with an ejection spring pretensioned to the maximum upon delivery or before the autoinjector is put into operation for a one-time ejection of the entire or at least a predetermined content of the product container. Accordingly, the autoinjector does not have a dose selection mechanism. A pre-filled disposable ready-to-use syringe comprises the product container and an injection needle non-detachably fastened thereto and is held axially fixedly in the housing of the autoinjector. The autoinjector, or at least the ready-to-use syringe and the syringe holder, are accordingly provided only for one-time use.

In addition to the processor unit for evaluating the data from the sensor, the electronics module can also comprise a Bluetooth transmitting device for wireless transmission of information about the ejection. The transmitting device is designed for repeated transmission of the preferably suitably encrypted information together with a non-encrypted, unique identifier of the autoinjector. The transmitting device preferably and exclusively operates as a beacon in a Bluetooth broadcast mode and communicates the information and the identifier in the form of advertising packets.

Another aspect of the invention relates to the modular design of a device family or platform having two autoinjectors which have as many identical or interchangeable components as possible and of which only a first autoinjector has an electronics module. A device family according to the invention thus comprises a first and a second autoinjector, both with the same elongated device housing for gripping and holding the autoinjector by a user, the same syringe holder for receiving a pre-filled syringe, the same advancing element for ejecting a dose by advancing a piston in the syringe, the same trigger mechanism for triggering the ejection, and the same needle protection sleeve for lateral covering of the needle after ejection. At the proximal end, the first autoinjector has a module housing for covering an opening of the device housing which accommodates an electronics module and can be detached from the device housing. At the proximal end, the second autoinjector has an end or closing cap for covering the opening of the device housing, which is permanently and non-detachably or respectively not non-destructively connected to the device housing, preferably snapped, welded, or glued. Another difference is that the first autoinjector, in addition to the electronics module with a sensor and communication unit, has a release element. In a locking position, the release element locks or blocks a loosening movement of the module housing prior to the start of the ejection. Preferably, the first auto-injector also has a housing insert which is connected to the proximal end of the device housing in a form-fit, rotationally and axially fixed manner and is used as a module adapter for the electronics module, the release element and/or the module housing.

Preferably, the device family comprises a third autoinjector which is identical to the first autoinjector except for the fact that the module housing of the third autoinjector is not intended to be separated from the device housing or respectively the housing insert by the user. The module housing and/or the housing insert of the third autoinjector therefor have differently shaped snap or connecting elements than the module housing and/or the housing insert of the first auto-injector. In particular, the third autoinjector likewise has a release element, even if this is not used or is obsolete due to the said non-detachable connecting elements. In this case, the electronics module is disposed of together with the third autoinjector.

Preferably, the needle protection sleeve springs for moving the needle protection sleeve into a needle protection position and the ejection springs of the two autoinjectors are also identical. However, the lack of drive of a release element in the second autoinjector can also accept a spring dimensioned with less margin.

BRIEF DESCRIPTION OF THE DRAWINGS

Preferred embodiments of the invention are described below in connection with the appended figures. These embodiments are intended to show basic possibilities of the invention and are in no way to be interpreted as limiting. In the drawings.

DETAILED DESCRIPTION

Definitions

The term "product," "medicament," or "medical substance" in the present context includes any flowable medical formulation which is suitable for controlled administration by means of a cannula or hollow needle in subcutaneous or intramuscular tissue, for example a liquid, a solution, a gel, or a fine suspension containing one or more medical active ingredients. A medicament can thus be a composition with a single active ingredient or a premixed or co-formulated composition with a plurality of active ingredients from a single container. The term includes in particular drugs, such as peptides (e.g., insulins, insulin-containing medicaments, GLP-1-containing preparations as well as derived or analogous preparations), proteins and hormones, biologically obtained or active ingredients, active ingredients based on hormones or genes, nutrient formulations, enzymes, and other substances both in solid (suspended) or liquid form. The term also includes polysaccharides, vaccines, DNA or RNA or oligonucleotides, antibodies or parts of antibodies as well as suitable base substances, excipients, and carrier substances.

The term "distal" refers to a side or direction directed toward the front, piercing-side end of the administration apparatus or toward the tip of the injection needle. In contrast, the term "proximal" refers to a side or direction directed toward the rear end of the administration apparatus that is opposite the piercing-side end.

In the present description, the term "injection system" or "injector" is understood to mean an apparatus in which the injection needle is removed from the tissue after a controlled amount of the medical substance has been dispensed. In contrast to an infusion system, the injection needle in an injection system or in an injector thus does not remain in the tissue for a longer period of several hours.

Figure 1:
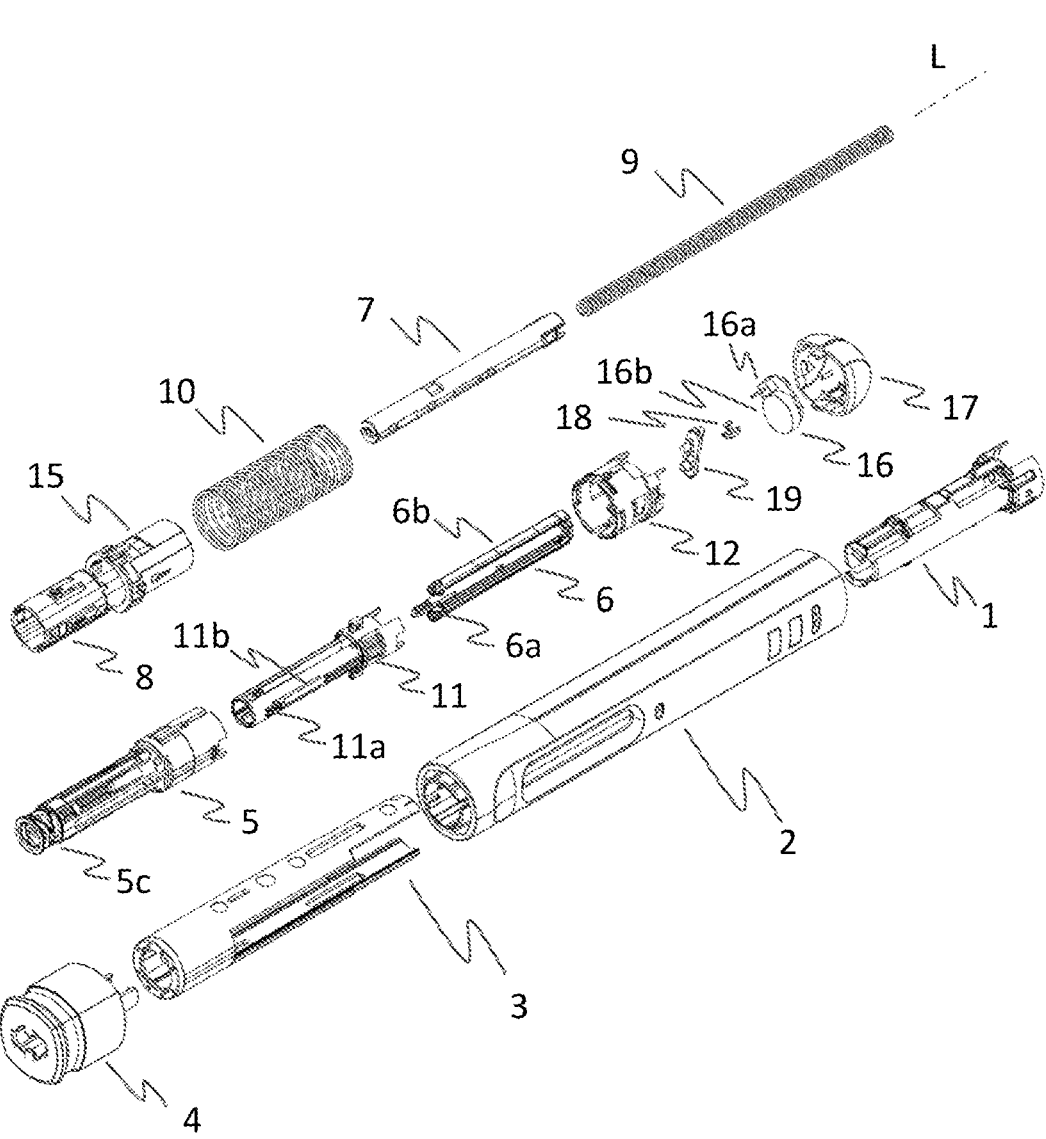
FIG. 1 shows an exploded view of an autoinjector with a compression spring drive.

FIG. 1 shows an exploded view of an autoinjector comprising a drive having a compression spring designed as a spiral coiled spring. The autoinjector has a sleeve-shaped, elongated injector or device housing 2 having a longitudinal axis L, which is held in one hand by a user during the injection. A pre-filled syringe (not shown) is accommodated in a syringe holder 1, which in turn is snapped into the housing 2 in a rotationally and axially fixed manner. In the as-delivered state, a pull-off cap 4 is arranged at the distal end of the housing 2, which is removed before using the auto-injector. A needle protection sleeve 3 can be displaced relative to the housing 2 and along the longitudinal axis L by an actuating stroke $H_B$ in the proximal direction into an actuated position in order to trigger a product ejection. A mechanism holder 5 is snapped into the housing 2 in a rotationally and axially fixed manner and presses the pre-filled syringe distally into the syringe holder 1 by means of a retaining spring section 5c.

The autoinjector has an ejection spring 9 in the form of a spiral coiled spring acting as a compression spring, which in the as-delivered state is almost completely surrounded by a sleeve-shaped advancing element 7 and exerts a force on the latter in the distal direction. The proximal end of the ejection spring 9 is supported on a retaining element 6, which has two arms 6b, wherein an engagement element 6a is arranged on each arm 6c. The engagement elements 6a point radially towards the longitudinal axis L and, in the as-delivered state, engage in recesses on the outer surface of the advancing element 7. A switching module with a switching sleeve 15 and a locking sleeve 8 prevents the two arms 6b from deflecting, as a result of which a movement of the advancing element 7 relative to the retaining element 6 in the distal direction is also prevented. The switching sleeve 15 is connected to the proximal end of the needle protection sleeve 3 at least with a force-fit and is pushed distally by a needle protection spring 10. To trigger the ejection, the needle protection sleeve 3 and the switching module 15, 8 are moved proximally, whereby the needle protection spring 10 is tensioned and the arms 6b can deflect. As a result, the axially fixed coupling between the advancing element 7 and the retaining element 6 is removed, and while the former is moved distally, the retaining element 6 can be displaced proximally by a small initial stroke up to an axially fixed stop. When the autoinjector is removed from the injection site, the needle protection sleeve 3 is moved distally by the needle protection spring 10 and locked in a needle protection position by the switching module 15, 8.

The needle protection spring 10 is a spring made of metal which acts as a compression spring and is designed as a spiral coiled spring and is supported with its proximal end on a signal element 11. In the as-delivered state, the signal element 11 is in contact with a signal stop of a housing insert 12, and has two arms 11b, wherein an engagement element 11a is arranged on each arm 11b. The engagement elements 11a point radially towards the longitudinal axis L and, in the as-delivered state, engage in further recesses of the advancing element 7. At the beginning of the ejection, the signal element 11 is thereby moved away from the signal stop 12a by a clamping stroke, then held in engagement with the locking sleeve 8 by the outer surface of the advancing element, and released at the end of the ejection for a movement accelerated by the needle protection spring 10 proximally towards the signal stop 12a. Details regarding the design of the autoinjector with a compression spring drive are described in the patent application WO 2021160540 A1.

The housing insert 12 is connected in a form-fit, rotationally and axially fixed manner to the proximal end of the housing 2 and can also axially supplement or extend it and can generally be used as a module adapter for an electronics module housing or device end cap. At the proximal end of the housing insert 12, a detachable module housing 17 is provided for an electronics module 16. The electronics module 16 comprises a sensor 16a and a battery 16b, and further comprises a processor unit, a communication unit, and/or a light source for optical signaling of an operating state. The sensor 16a is designed to detect or monitor the presence of the signal element 11 in its proximal position in contact with the signal stop 12a, or the absence of the signal element from this position for the duration of the ejection. The sensor 16a of the electronics module 16 is designed as a switching detector, the sensor 16a and/or the signal element 11 have an axial projection in the form of a plunger in order to ensure a mutual force fit. Alternatively, a switching adapter can be provided as a separate component for transmitting the position of the signal element 11 to the switching detector via an axial, tilting or other deflection movement. A processor of the electronics module 16 evaluates the detected movements of the signal element and, in particular, reports the time of a successful injection via a communication module.

Figure 2A:
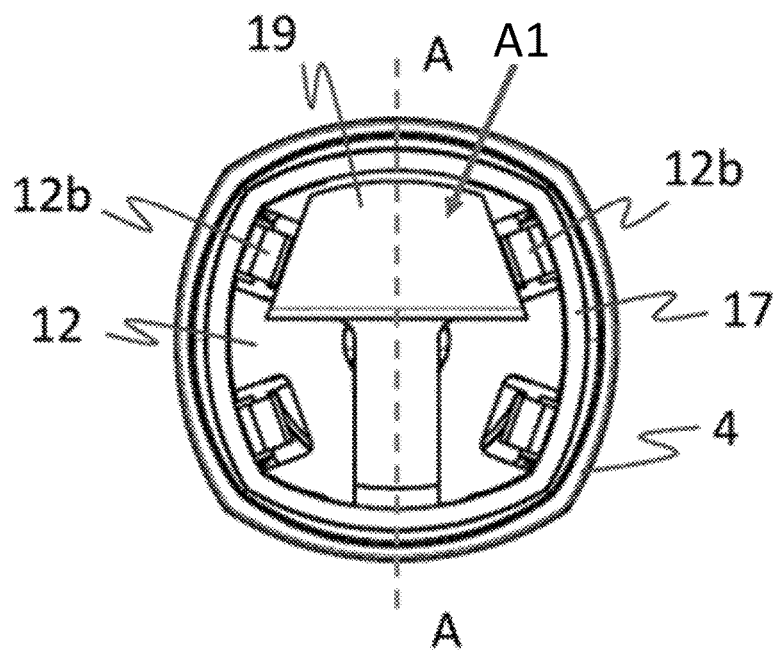
FIGS. 2A and 2B show a first embodiment of the securing mechanism.
Figure 2B:
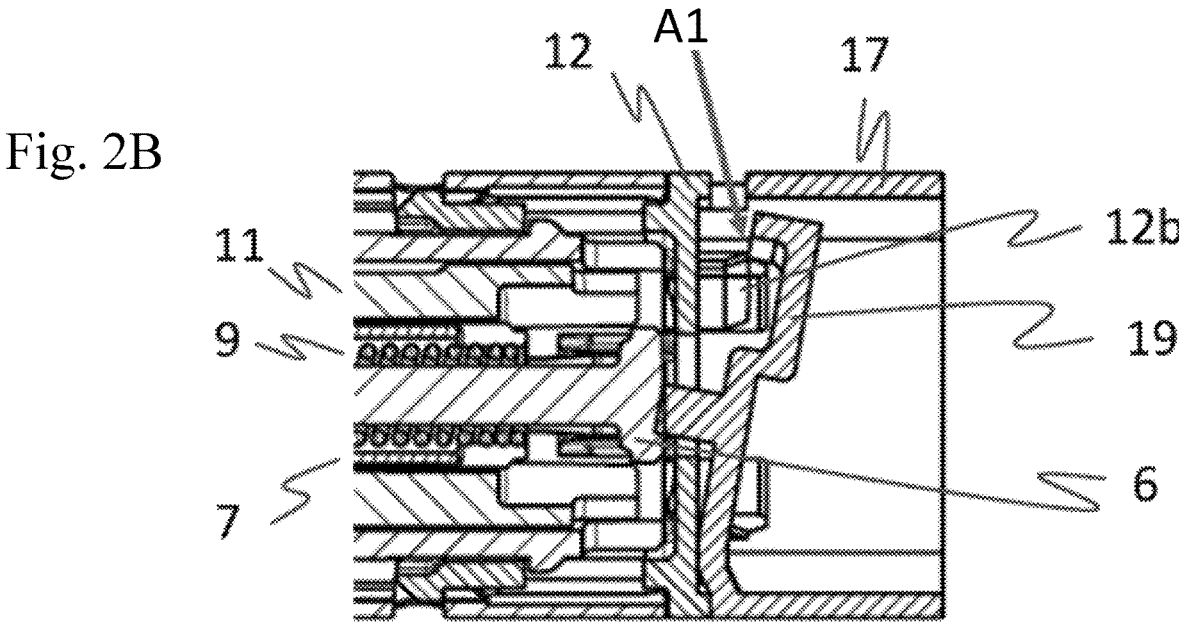

FIG. 2A shows an axial view of the autoinjector from behind with the module housing 17 cut off and without the electronics module, and FIG. 2B shows a detail of a longitudinal section through a plane A-A of FIG. 2A. In this embodiment of the invention, the module housing 17 is fastened to the housing insert 12 by means of a snap connection. Two flexible snap elements 12*b* on the housing insert engage behind radially inwardly projecting projections of the module housing 17 and are prevented from deflecting inwards by a release element 19 in the form of a bending arm on the module housing. Due to the small initial stroke of the retaining element 6 in the proximal direction, the release element 19 is deflected or respectively bent and the snap elements 12*b* released, so that the module housing 17 can now be removed axially backwards from the housing insert by the user.

The functions and properties of the housing insert can also be taken directly from the housing of the injection device; a separate but fixedly connected housing insert is primarily advantageous for manufacturing reasons. Accordingly, the snap elements can also be provided on the housing of the injection device, or can also be attached to the module housing and snap into openings in the housing. In addition, in this concept, the module housing can be separated by means of a screwdriver or similar tool. For this purpose, the screwdriver is guided in the direction of the arrow A1 through an opening in the module housing under an elastic end of the release element and tilted. The release element can also be a separate component and can be moved backwards as a whole by the retaining element. As a result, the release element is not bent and can also release diagonally opposite snap elements.

Figure 3A:
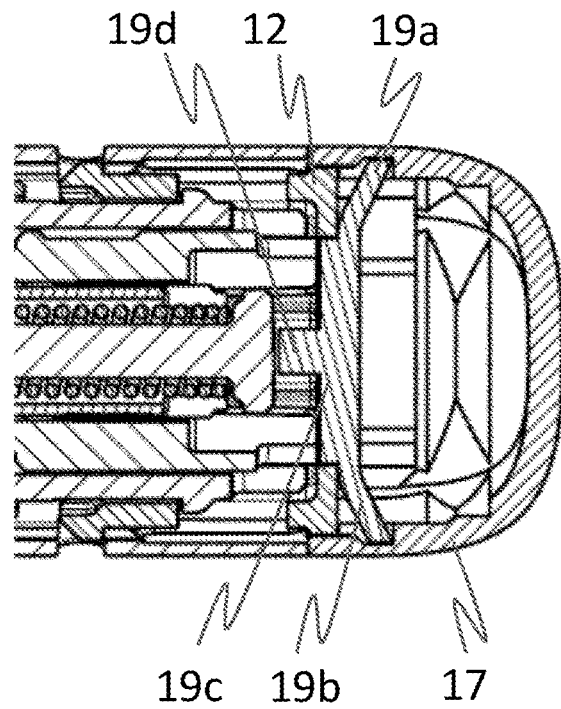
FIGS. 3A and 3B show a first variant of a second embodiment of the securing mechanism.
Figure 3B:
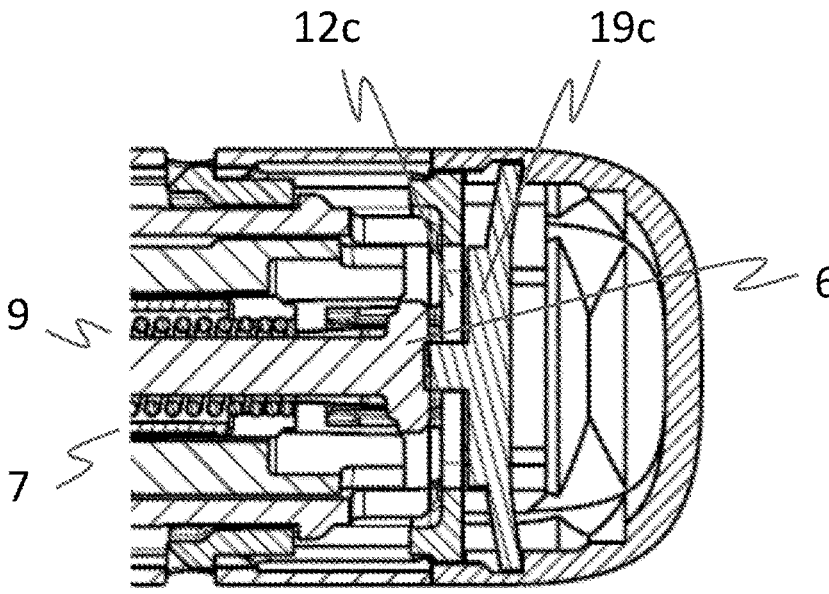

FIGS. 3A and 3B show a longitudinal section of a first variant of a second embodiment of the invention, in which the module housing can be released by means of a rotational movement. A release element 19 is anchored in the module housing 17 in a rotationally fixed manner via two diagonally opposite anchorings 19*a* and is pretensioned distally via two spring arms 19*b*, so that in the locking state (FIG. 3A) a rounded rectangular locking profile 19*c* of the release element 19 engages in a matching profile receptacle 12*c* of the housing insert 12. A pin-shaped distal protrusion or continuation 19*d* of the release element strikes the proximal end of the retaining element 6 and is pushed proximally by the initial stroke thereof against the pretension of the spring arms 19*b*, whereby the locking profile 19*c* is moved out of the recess 12*c*, and the release element 19 can be rotated with the module housing 17 (FIG. 3B).

Instead of the rectangular locking profile, any profile that is non-rotationally symmetrical about the longitudinal axis L can be used for receiving a torque, for example a cross or a star shape, or a profile with a plurality of embossments for engagement in a plurality of indentations. The locking profile can comprise a distally projecting structure on the release element for engaging in a recess on the housing insert, or a proximally projecting bulge on the housing insert for engaging in a corresponding indentation on the release element. Instead of the spring arms, separate spring elements can be provided for the distal pretensioning of the release element, and thus prevent a spontaneous release of the loosening movement, or the release element is connected in a force-fit to the retaining element via the pin-shaped distal continuation. The rotating loosening movement of the module housing relative to the device housing can be followed by an axial loosening movement similar to a bayonet lock, or the rotational movement is part of a screwing loosening movement.

Figure 4A:
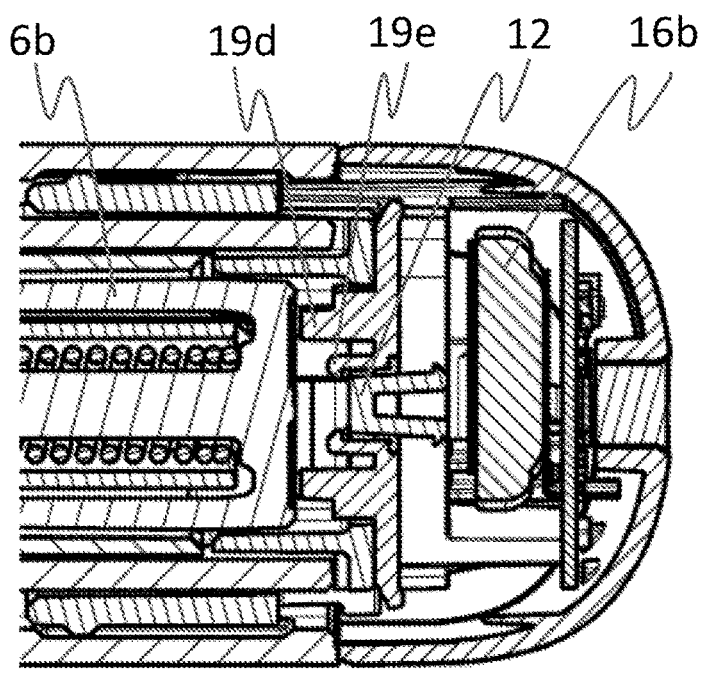
FIGS. 4A and 4B shows a second variant of the second embodiment.
Figure 4B:
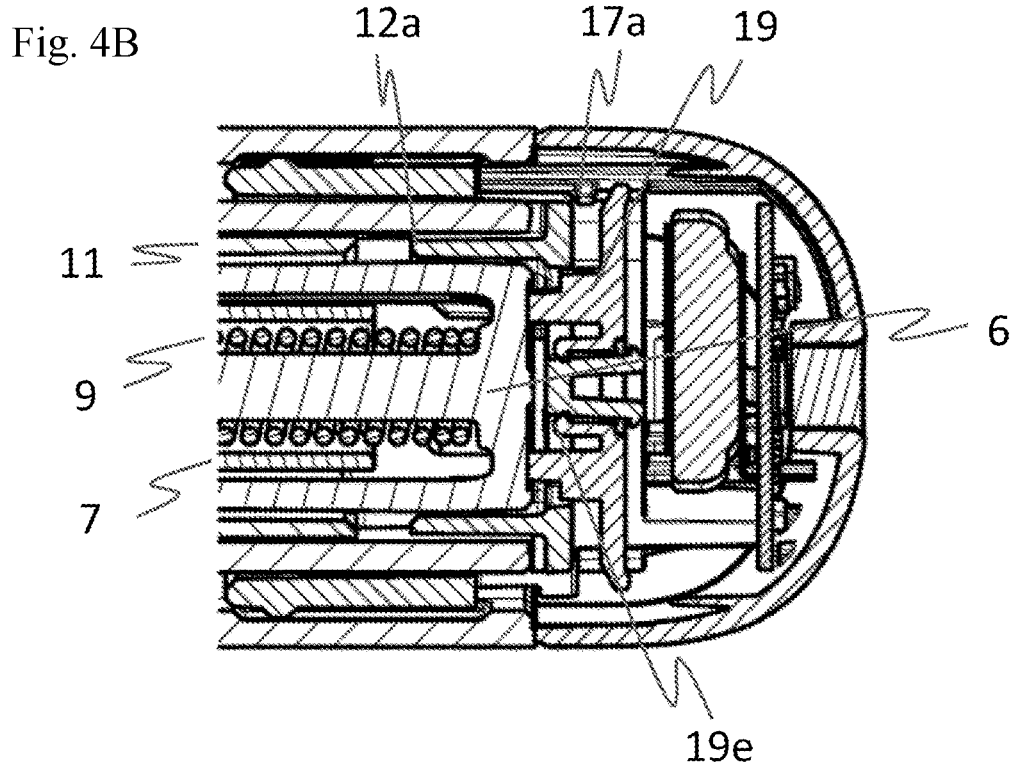

FIG. 4A shows a longitudinal section of a second variant of the second embodiment of the invention in the as-delivered state, FIG. 4B shows the second variant of the second embodiment in the triggered state. The sectional plane is rotated by 90° relative to that in FIGS. 3A and 3B, as a result of which the arms 6*b* of the retaining element 6 can also be seen next to a central pin. In the as-delivered state, the release element 19 is held on the housing insert 12 by means of catches 19*e*. The catches 19*e* replace the spring arms of the first variant and are able to hold at least the dead weight of the release element 19 against a movement in the proximal direction into a release position of the release element. After triggering, the ejection spring 9 pushes, via the continuations 19*d*, the release element 19 proximally and thus the catches 19*e* out of their retaining position. Opposite peripheral ends of the release element are moved axially away from cams 17*a* and release them for a rotational movement. Alternatively or complementary thereto, as in the previous variant, a rotation blockage is possible by means of a profile receptacle and locking profile.

Figures 5A, 5B:
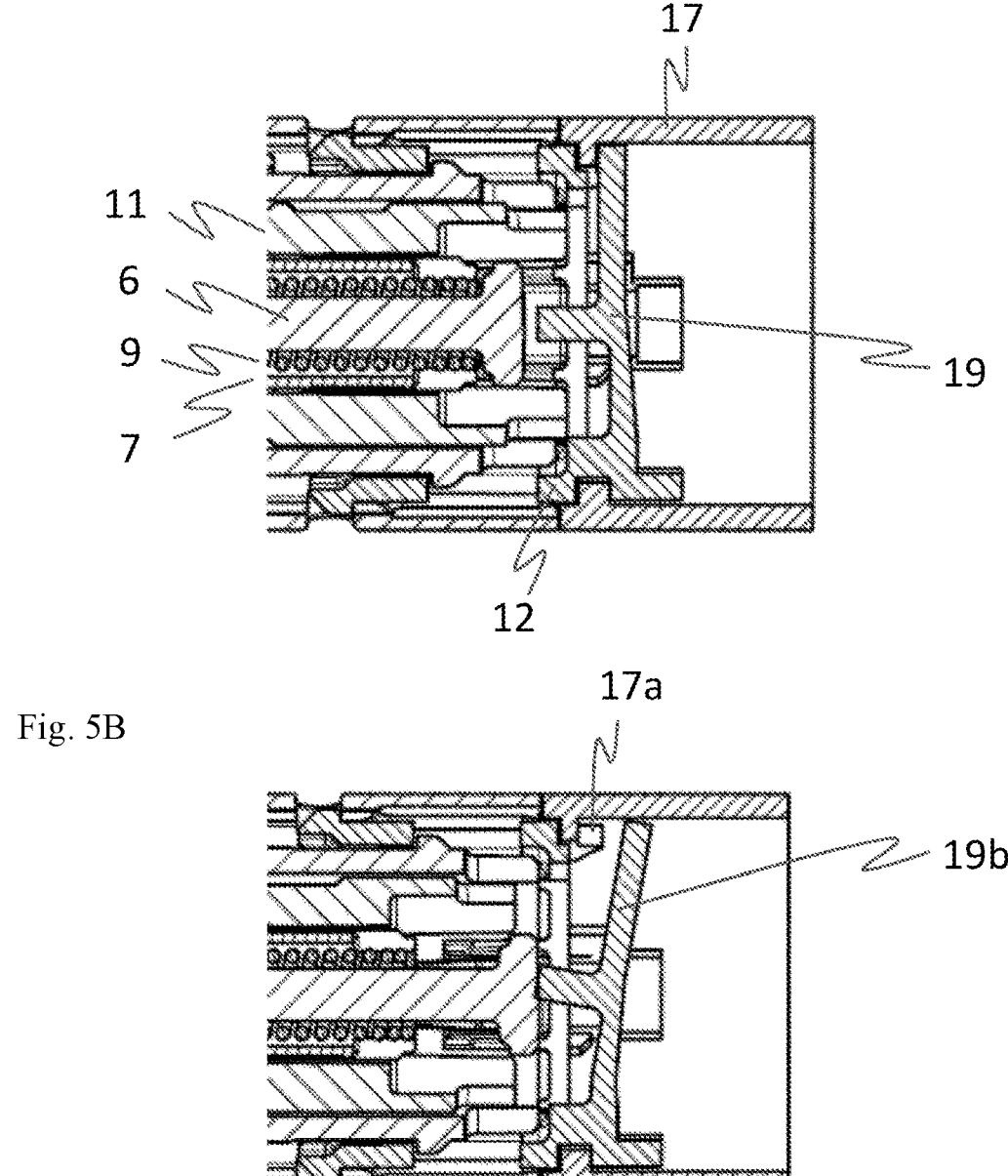
FIGS. 5A and 5B show a third variant of the second embodiment.

FIG. 5A shows a longitudinal section of a third variant of the second embodiment of the invention in the as-delivered state, and FIG. 5B shows the third variant of the second embodiment in the triggered state in which the release element 19 is formed integrally with the housing insert 12 and thus does not itself rotate during the rotating loosening movement. The release element 19 is therefore not a separate component and thus cannot fall out and be lost at the moment the module housing 17 is removed. As in the first embodiment, the release element 19 is elastically or flexibly hinged and connected to the housing insert on one side. The opposite end of the spring arm 19*b* is in a rotationally locking stop with a radially inwardly projecting cam 17*a* of the module housing 17. The end of the spring arm 19*b* is raised proximally by the initial stroke of the retaining element 6 and the cam 17*a* is released for rotation.

Figure 6:
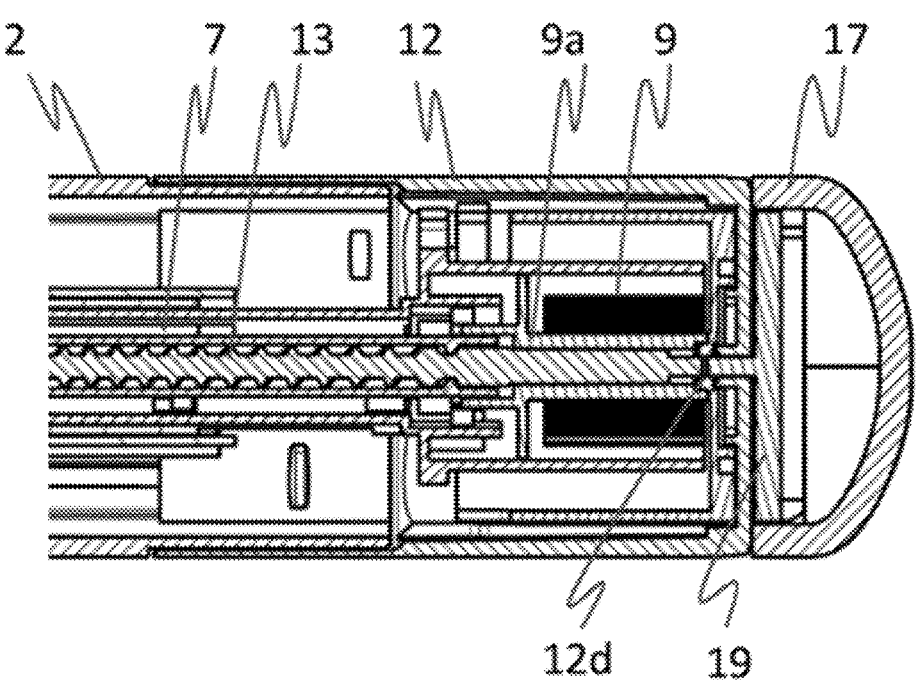
FIG. 6 shows a partial longitudinal section of an autoinjector with torsion spring drive.
Figure 8A:
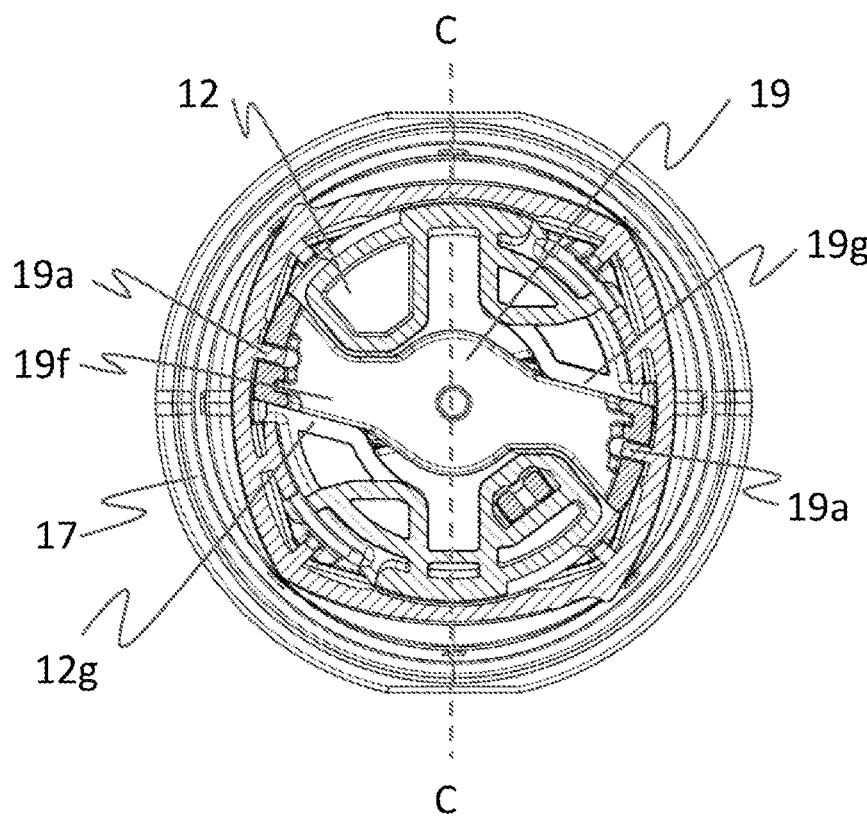
FIGS. 8A and 8B show a fourth variant of the second embodiment.
Figure 8B:
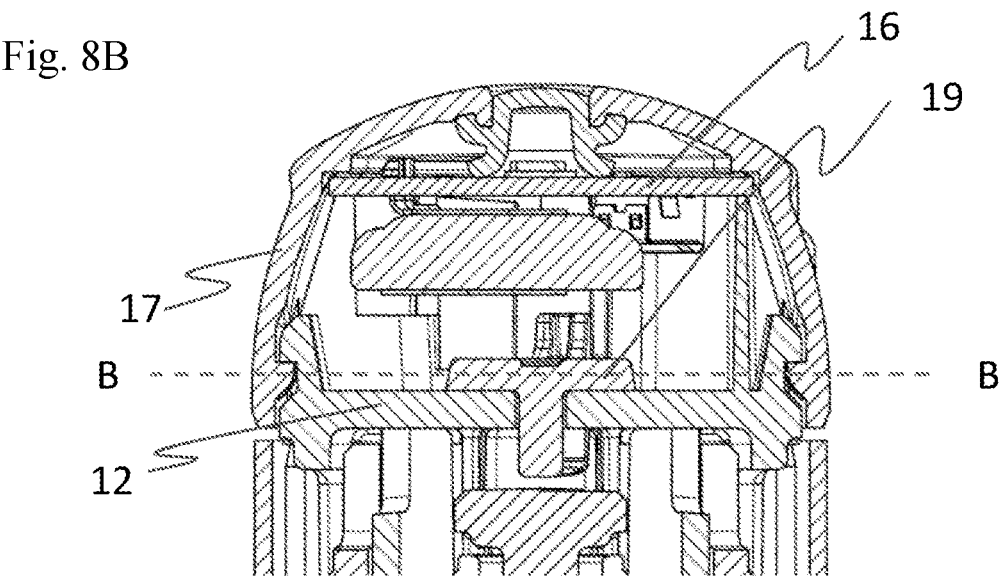

FIG. 8A shows a cross-section, and FIG. 8B shows a longitudinal section of a fourth variant of the second embodiment of the invention in the as-delivered state, with indication of the corresponding sectional plane B-B and C-C. The release element 19 is permanently anchored or guided in the module housing 17 in a rotationally fixed manner via two diagonally opposite anchorings 19*a*, both in the as-delivered state shown and after the release movement of the release element in the proximal direction has been carried out. Exclusively in the as-delivered state, two rigid legs 19*f* of the release element rest, each via a radially extended contact surface 19*g*, in a force-fit manner against locking or counter-contact surfaces 12*g* of the housing insert 12, and are thereby prevented from rotating in the counter-clockwise direction (when viewed distally, FIG. 8A). The radial extension of a contact surface 19*g* is at least one third, preferably at least half the length of the leg 19*f*, and thereby distributes the force acting on the housing insert in the event of a rotation attempt before the release. When the electronics module 16 is separated by means of a distal limitation of the mobility in the module housing 17 or by means of a proximal limitation of the mobility in the housing insert 12, the release element can remain in the electronics module or in the autoinjector. FIG. 6 shows a longitudinal section of the proximal end of an autoinjector comprising a drive with a torsion spring designed as a spiral spring and otherwise largely functionally identical components as in the second embodiment. The autoinjector comprises a housing 2, a housing insert 12 fixedly connected to the housing, a drive element 13 in the form of a threaded rod, an advancing element 7 in the form of a sleeve with an internal thread in engagement with the thread of the threaded rod, and an ejection spring 9 in the form of a drive or spiral spring. The latter is wound onto the shaft of a spring coil 9a and connected thereto in a rotationally fixed manner with an inner end. The spring coil 9a, in turn, is coupled to the drive element 13 in a rotationally fixed but not axially fixed manner. A needle protection sleeve also serves as a triggering element for triggering the product ejection, wherein a switching module coupled axially to the needle protection sleeve releases a retaining element, thereby enabling the axial advancement of the advancing element 7 or the rotation of the drive element 13 or the spring coil 9a. After triggering the ejection, the advancing element 7 is brought into abutment with the stopper of the syringe, whereupon a counter pressure builds up in the liquid of the syringe on the stopper, briefly blocking the longitudinally guided advancing element 7 and thereby screwing the rotating threaded rod as drive element 13 proximally. As soon as the threaded rod itself comes to rest with a shoulder against a distally directed stop 12d, the counter pressure is overcome and the advancing element 7 completes the ejection stroke. The proximal movement of the drive element 13 is comparable to the initial stroke of the retaining element of the compression spring embodiments and is sufficient for an axial release movement of the release element 19.

Alternatively, a proximal end face of a proximal flange of an axially fixed spring coil can have a non-continuous, rotationally symmetrical structure with at least one plateau projecting proximally and/or an axial recess. A distally extending continuation of the release element, which is radially offset from the axis and is in a distal position in the recess before the ejection is triggered, is lifted onto said plateau or pushed proximally by the rotation of the spring coil, and held in this proximal release position by means of suitable catches. Instead of a plateau in the form of a sector, a radially aligned, proximally projecting rib can also provide the axial deflection of the release element.

Details of the design of the autoinjector with torsion spring drive and of a rotation sensor for alternating continuous detection of at least two rotational positions per revolution of the drive element during the ejection are disclosed in patent application WO 2021191095 A1.

Figure 7:
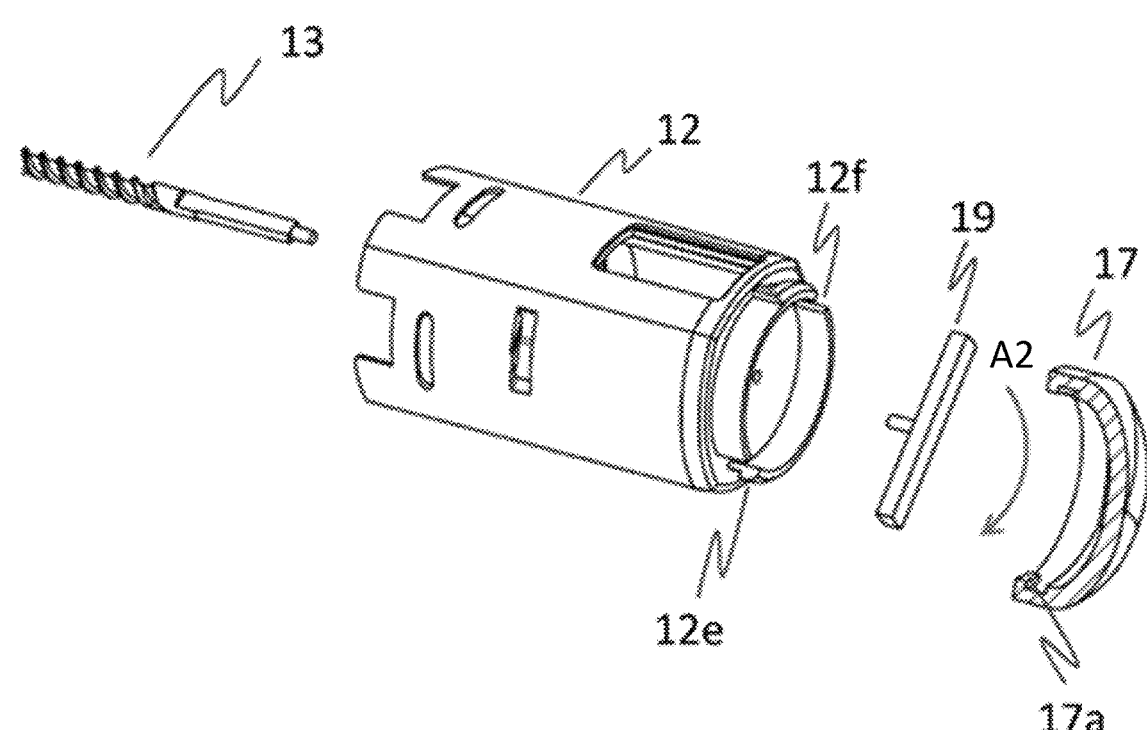
FIG. 7 shows a third embodiment of the securing mechanism.

FIG. 7 shows an exploded view of four components of the embodiment from FIG. 6 with a bayonet lock between the module housing 17 and the housing insert 12. The module housing 17 is additionally cut along the longitudinal axis. The separating movement thus comprises a rotation of the module housing relative to the housing insert 12 in the direction of rotation indicated by the arrow A2. For this purpose, the housing insert 12 has a rotary guide 12e on an outer side for a cam 17a on the inside of the module housing 17. The starting position of the cam 17a in the rotary guide 12e is delimited by a slot-shaped axial guide 12f, through which an end of the release element 19 projects. The latter is axially coupled to a proximal end of the drive element 13 and is raised by at least the axial extension of the cam 17a by the proximal movement of the drive element 13. The module housing shown comprises two cams 17a, each with an angular extension of approximately 45°, wherein up to four pairs of rotary guides/cams are possible with an angular extension of less than 45°.

As an alternative to the described proximal movement of the drive element, a rotational movement of the threaded rod can be converted into an axial movement of the release element via a threaded engagement with the release element. For this purpose, the threaded rod and the release element have a thread overlap corresponding to the release stroke of the release element, so that the release element can be moved from the engagement with the threaded rod at the end of the proximal movement and can be moved axially away therefrom. A flexible release element acting on one side, as in FIGS. 5A and 5B, which is fixedly connected to the housing insert 12 or the module housing 17 on one side, is also conceivable.

Further alternatively, the proximal movement of the release element can be caused by a final stroke of the retaining element or a signaling element as described above at the end of the ejection. However, a signaling element without initial or loading movement is particularly suitable, i.e., with only a signaling movement against a stop at the proximal end of the autoinjector, such as, for example, a signaling element on which the ejection spring is supported proximally and which is released from the proximal end of the advancing element for a signaling movement in the proximal direction at the end of the ejection.

| List of reference signs | |
|---|---|
| 1 | Syringe holder |
| 2 | Housing |
| 3 | Needle protection sleeve |
| 4 | Pull-off cap |
| 5 | Mechanical holder |
| 5c | Retaining spring portion |
| 6 | Retaining element |
| 6a | First engagement element |
| 6b | Arm |
| 7 | Advancing element |
| 8 | Locking sleeve |
| 9 | Ejection spring |
| 9a | Spring coil |
| 10 | Needle protection spring |
| 11 | Signal member |
| 11a | First engagement member |
| 11b | Arm |
| 12 | Housing insert |
| 12a | Signal stop |
| 12b | Snap element |
| 12c | Recess |
| 12d | Stop |
| 12e | Rotary guide |
| 12f | Axial guide |
| 12g | Locking surface |
| 13 | Drive element |
| 14 | Needle protection cap |
| 15 | Switching sleeve |
| 16 | Electronics module |
| 16a | Sensor |
| 16b | Battery |
| 17 | Module housing |
| 17a | Cam |
| 18 | Switching adapter |
| 19 | Release element |
| 19a | Anchoring |
| 19b | Spring arm |
| 19c | Locking profile |
| 19d | Continuation |
| 19e | Catch |
| 19f | Leg |
| 19g | Contact surface |

What is claimed is:

1. An injection device for subcutaneously administering a maximum content of a product container through a cannula at a distal end of the product container, comprising:

a device housing having an opening at a proximal end;

a module housing for covering the opening and configured to be separable from the device housing by a separating operation;

a drive arranged in the device housing for moving an advancing element and for a one-time automatic ejection of the content of the product container;

an electronics module arranged in the module housing comprising a sensor configured for detecting the automatic ejection; and a mechanical securing mechanism for enabling the separating operation as, or after, the automatic ejection is triggered.

2. The injection device according to claim 1, wherein the separating operation comprises a rotating loosening movement of the module housing relative to the device housing, and/or an axial loosening movement of the module housing towards the device housing and/or away from the device housing.

3. The injection device according to claim 2, wherein the mechanical securing mechanism comprises a release element configured for locking the loosening movement prior to triggering the automatic ejection in a locking position of the release element, and for releasing the loosening movement prior to removing the injection device from an injection site in a release position of the release element.

4. The injection device according to claim 3, wherein the injection device comprises an ejection spring for driving the advancing element, and a retaining element for retaining the ejection spring in a pretensioned state prior to release, or a drive element for transmitting an ejection force of the ejection spring to the advancing element, wherein the release element is moved into the release position by a proximal movement of the retaining element or of the drive element.

5. The injection device according to claim 3, wherein the separating operation comprises the axial loosening movement, and the module housing is snapped by snap elements configured to be prevented from loosening by the release element in the locking position.

6. The injection device according to claim 3, wherein the separating operation comprises the rotating loosening movement, and the release element in the locking position prevents a radial projection on the module housing from rotating or is prevented from rotating by the radial projection.

7. The injection device according to claim 3, wherein the separating operation comprises the rotating loosening movement, and the release element is coupled to the module housing in a rotationally fixed manner and is prevented from rotating by a radially extended force-fitting contact surface in contact with a locking surface.

8. The injection device according to claim 1, wherein the electronics module comprises a battery for supplying power to a communication unit of the electronics module, wherein the battery is removable from the electronics module only when the module housing is separated.

9. The injection device according to claim 1, further comprising an ejection spring for driving the advancing element, and a retaining element for retaining the ejection spring in a pretensioned state prior to release, or a drive element for transmitting an ejection force of the ejection spring to the advancing element, wherein the sensor detects an axial or radial movement of at least one of the advancing element, the retaining element, or the drive element, caused by the ejection spring.

10. The injection device according to claim 1, further comprising a needle protection spring configured for driving a needle protection sleeve distally and/or a signal element proximally, wherein the sensor detects an axial movement of the needle protection sleeve or of the signal element caused by the needle protection spring.

11. The injection device according to claim 1, wherein the injection device is configured as an autoinjector with a maximum pretensioned ejection spring for the one-time automatic ejection of an entire content, or at least a predetermined content, of a pre-filled syringe.

12. The injection device according to claim 11, wherein the autoinjector is a first autoinjector, and further comprising a second autoinjector, the second autoinjector comprising a second device housing identical to the first autoinjector and having an opening at a proximal end, an identical drive to the first autoinjector, and a closing cap non-detachably connected to the second device housing for covering the opening at the proximal end of the second device housing.

13. The injection device according to claim 12, wherein the first autoinjector further comprises a housing insert configured to be coupled in a rotationally and axially fixed manner to the proximal end of the device housing of the first autoinjector and serves as a module adapter for the module housing with the electronics module.

* * * * *